United States Patent [19]

Takeshita

[11] 4,228,922
[45] Oct. 21, 1980

[54] APPARATUS FOR INJECTING A DESIRED VOLUME OF LIQUID IN LIQUID AND GAS-LIQUID CHROMATOGRAPHY

[76] Inventor: Ryuzo Takeshita, No. 5-4-11, Koenji Minami, Suginami-Ku,Tokyo, Japan

[21] Appl. No.: 953,943

[22] Filed: Oct. 23, 1978

[51] Int. Cl.³ .......................... A61M 5/20; G01N 1/10
[52] U.S. Cl. .................................. 222/47; 73/425.4 P; 128/218 F
[58] Field of Search ....................... 222/41, 44, 47, 49, 222/50; 73/425.4 P, 425.6; 128/218 F, 215, 173 H

[56] References Cited

U.S. PATENT DOCUMENTS

| | | | |
|---|---|---|---|
| 2,472,116 | 6/1949 | Maynes | 128/218 F |
| 2,671,448 | 3/1954 | Harnisch | 128/218 F |
| 3,880,163 | 4/1975 | Ritterskamp | 128/218 F |
| 4,099,548 | 7/1978 | Sturm et al. | 73/425.6 X |

FOREIGN PATENT DOCUMENTS 12528 7/1903 Austria .................. 128/218 F

Primary Examiner—F. J. Bartuska
Attorney, Agent, or Firm—Stevens, Davis, Miller & Mosher

[57] ABSTRACT

An apparatus for liquid and gas-liquid chromatography, comprising a microliter syringe and a tubular holder wherein the syringe can be inserted. The holder is equipped with a spring system capable of moving a plunger of the syringe rapidly and a start button system capable of unlocking the locked spring.

3 Claims, 14 Drawing Figures

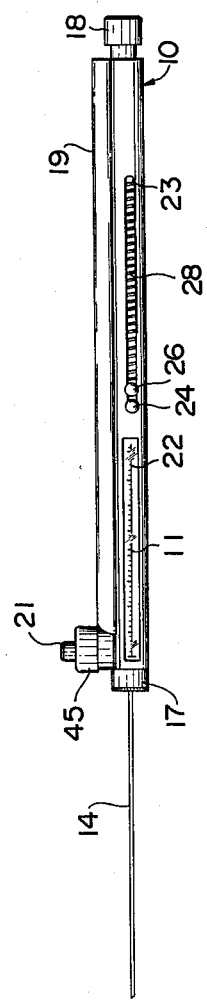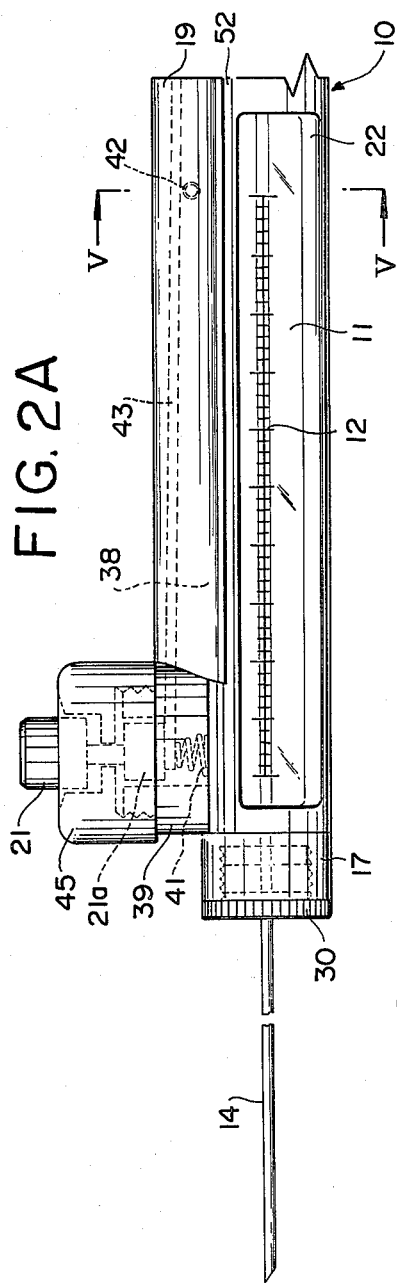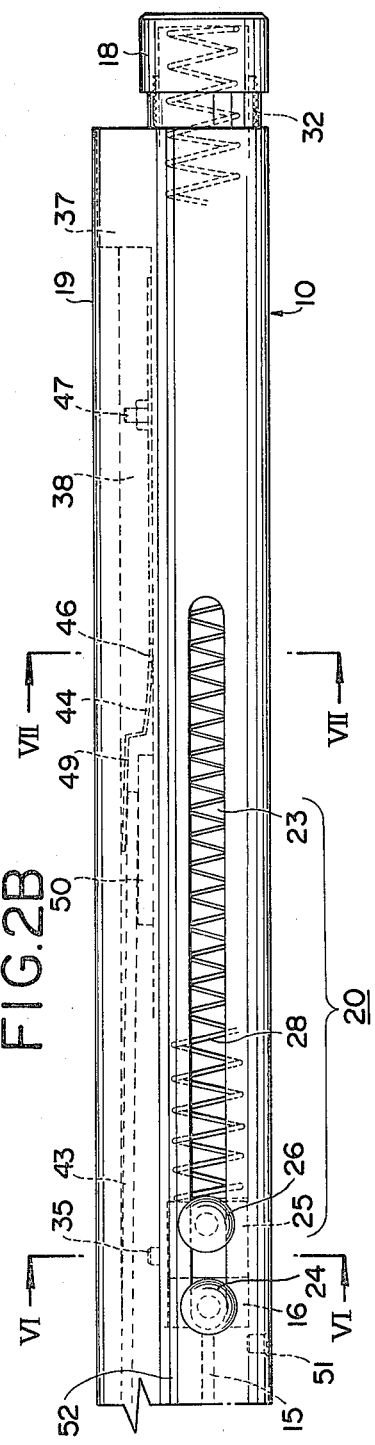

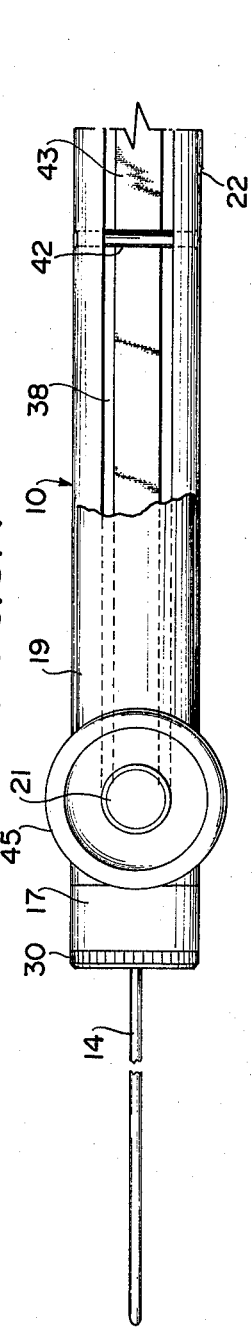
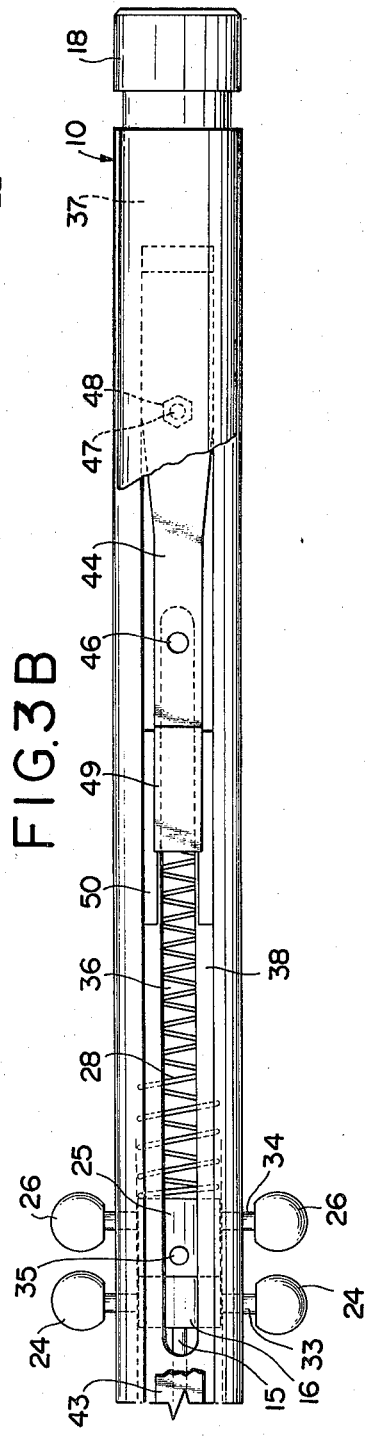
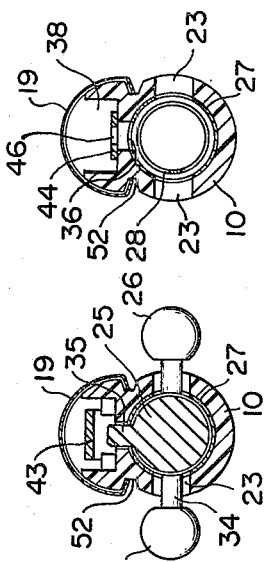
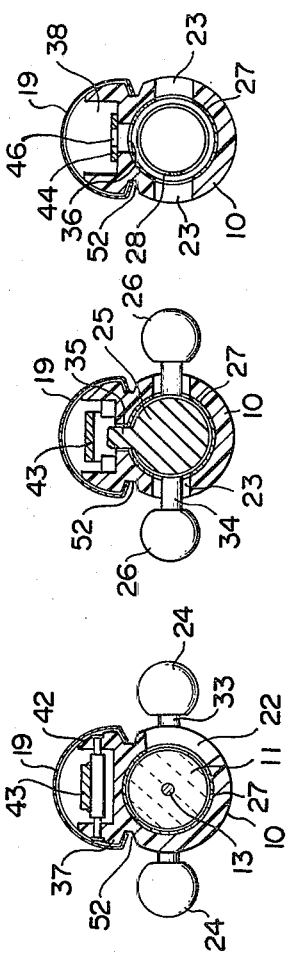
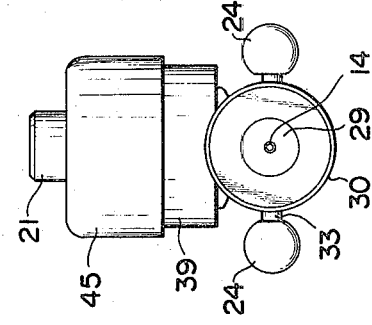

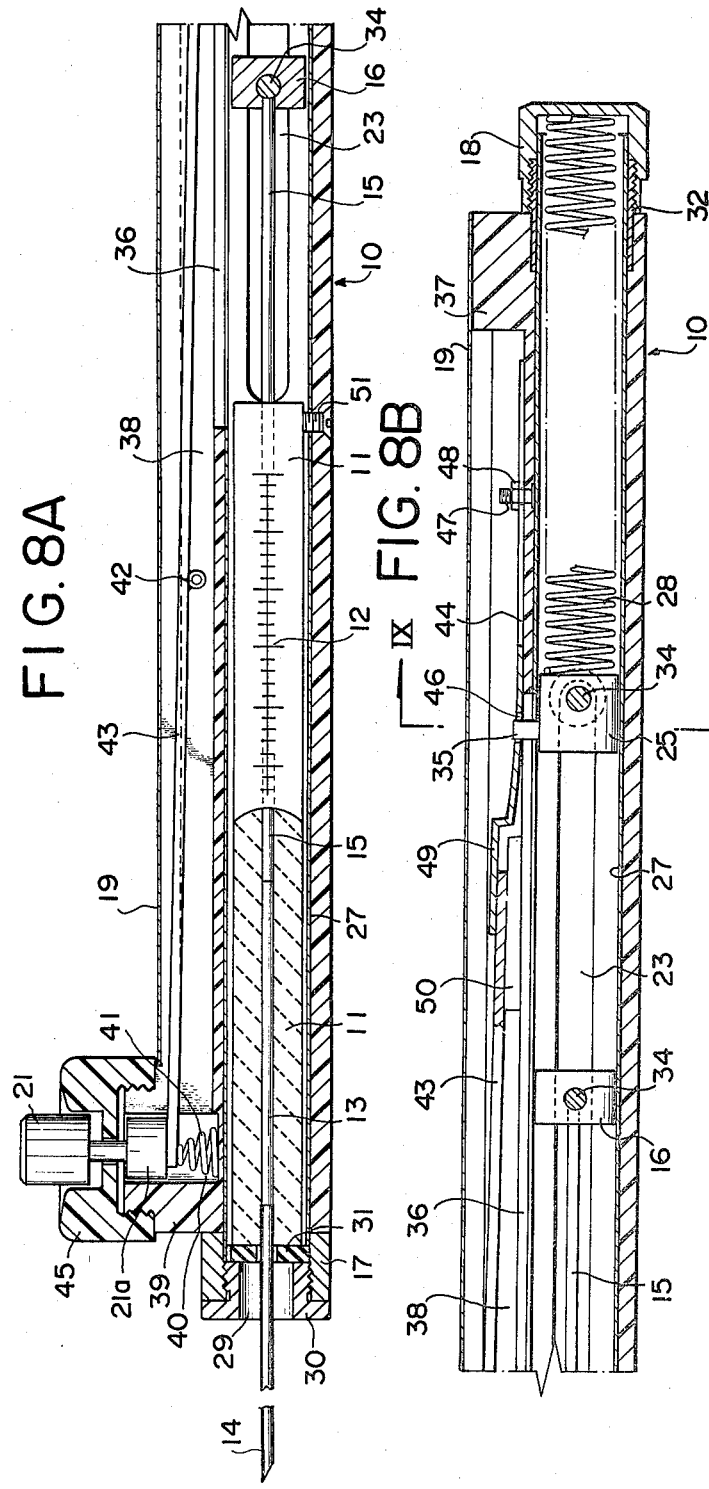

APPARATUS FOR INJECTING A DESIRED VOLUME OF LIQUID IN LIQUID AND GAS-LIQUID CHROMATOGRAPHY

This invention relates to apparatus for injecting a desired volume of a liquid sample in liquid and gas-liquid chromatography.

As for manual injection using a conventional microliter syringe, a desired volume of the liquid sample to be examined is filled into the syringe, and after the insertion of the needle through the rubber closure, the sample is discharged into the injection port of the chromatograph by pushing the plunger with a finger. Subsequently, the needle rapidly withdrawn.

In general, the conventional syringe has some avoidable faults as follows when used for the injection:

(1) In order to obtain a good separation of substances in the sample by liquid and gas-liquid chromatography, the sample should be discharged to be loaded on a column as rapidly and instantly as possible. When such operation is conducted by unskilful operators, the capillary plunger is often bent to be unable to use.

(2) So far as the plunger is pushed with the finger, the sample is always discharged with irregular force to cause ununiform residue of the sample in the needle of the syringe and give variation in the volume injected. Therefore in order to know the volume of the sample injected in quantitative analysis, an internal standard substances is usually used, having been dissolved in a concentration in the liquid sample.

(3) Because of the residual sample in the needle and barrel of the syringe after injection, the syringe is washed out with a solvent by pumps of the plunger. Thereafter the residual solvent is substituted with another sample prior to the injection of the sample. The pumps for the complete substitution at each step requires many times, because the residual sample or solvent in the syringe at each pump is apt to contact with the former end of the plunger and cannot be easily diffused owing to the capillary barrel of the syringe. Therefore the procedure makes the analysis by chromatography time consuming.

(4) When the syringe is filled as above to a desired volume of the sample, air in the needle is accompanied with the sample into the syringe. The pumping out the air from the syringe is needed for the sampling of the precise volume. Generally more than a few pumps can substitute the air with the liquid sample. Such operation is time consuming as above (3).

(5) As the syringe is grasped with one hand during the introduction of the sample to the syringe, the heat of the hand always causes variation of the measurements of the syringe.

In this convention, the plunger is always being pushed with more constant and stronger force by the spring than by the finger so that the syringe barrel becomes empty. With or without locking the spring, the syringe can be quickly ready for sampling and injecting a desired volume of the sample liquid.

When without locking the spring the syringe is overfilled with the sample by backing the plunger immersing the needle of the syringe in the sample and subsequently the plunger is kept apart from the fingers, the air introduced into the barrel can be almost put out at a time by the rapid advance of the plunger owing to elasticity of the spring. After the locking of the spring immersing the needle continuously in the sample, the plunger is backed. By bringing the plunger just to the scribe line of the volume according to the conventional sampling, a desired volume of the sample can be readily sampled into the syringe. As soon as the needle of the syringe is inserted being held with fingers of one hand through the rubber closure of the chromatograph, a start button is pushed down with a finger of the other hand holding the syringe. The needle is rapidly withdrawn.

A first object of this invention is to provide an injection apparatus which can quantitatively and promptly discharge a liquid sample.

Another object of this invention is to provide an injection apparatus in which upon depressing a start button of a holder, a spring is actuated so that the discharge of a sample liquid can be instantly completed with a constant force greater than the force of fingers.

Still another object of this invention is to provide an injection apparatus in which air entering a syringe in case of discharge a sample into the syringe is promptly expelled, the sample in a desired volume can be readily sampled, and the syringe after the injection of the sample can be washed very easily.

According to the invention, apparatus for liquid and gas-liquid chromatography, comprising a microliter syringe and a tubular holder wherein the syringe can be inserted. The holder is equipped with a spring system capable of moving a plunger of the syringe rapidly and a start button system capable of unlocking the locked spring.

In the injection using this invention apparatus, a desired volume of a liquid sample is filled into the syringe after locking the spring. Then the needle of the syringe is inserted through the rubber closure of chromatograph, a start button disposed at the end of the holder is pushed down and then the locked spring can be unlocked, resulting in discharging the volume rapidly. As the plunger is pushed with a uniform force by the spring, the liquid sample can be promtly discharged with a precise volume, inducing to good result in quantitative analysis.

In this injection, the sample can be discharged more instantly and constantly than in the hand injection, inducing to good separation of substances on the column equipped with the chromatograph and to good reproducibility in the volume injected. In addition, the syringe is inserted in the tubular holder composed of a stainless steel pipe and a molded product of plastics, so that the barrel of the syringe is always free from the heat of the hand not to cause the variation of the measurements, and the plunger is never bent in the pumps.

The washing of the syringe with a solvent after the injection and thereafter the transferring or sampling of another liquid sample into the syringe can be completely achieved with only twice pumps of the plunger withought locking the spring utilizing the elasticity of the spring, because little volume of the sample remains in the needle of the syringe by the stronger force of the spring than that of the finger.

These and other objects and many of the attendant advantages of this invention will be readily appreciated as the same becomes better understood by reference to the following detailed description when considered in connection with the accompanying drawings.

The explanation of the drawings is briefly described as follows:

FIG. 1 is a front view of an injection apparatus embodying the present invention;

FIG. 2A is an enlarged fron view of a fore half part of FIG. 1;

FIG. 2B is an enlarged front view of a hinder half part of FIG. 1;

FIG. 3A is a plan view corresponding to FIG. 2A;

FIG. 3B is a plan view corresponding to FIG. 2B;

FIG. 4 is a view of a left side in FIG. 2B;

FIG. 5 is a sectional view taken along line V—V in FIG. 2A;

FIG. 6 is a sectional view taken along line VI—VI in FIG. 2B;

FIG. 7 is a sectional view taken along line VII—VII in FIG. 2B;

FIG. 8A is an axial enlarged sectional view of the fore half part of the injection apparatus at the sampling of a liquid;

FIG. 8B is an axial enlarged sectional view of the hinder half part of the injection apparatus at the sampling of the liquid;

FIG. 9 is a sectional view taken along line IX—IX in FIG. 8B;

Figure 10A:
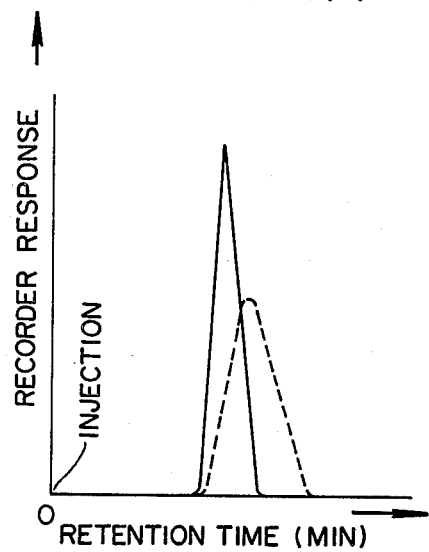
FIG. 10A shows chromatograms obtained by injecting a liquid containing a substance using the devised apparatus and conventional one.

The preferred embodiment is detailed as follows; The injection apparatus of this invention is shown in FIG. 1. Referring to FIGS. 1, 2A and 2B, the front end of a tubular holder 10 has an end ring 17, while the rear end thereof is closed by a box nut 18. A semi-cylindrical cover 19 is disposed on the holder 10. A microliter syringe 11 is inserted in the fore half part of the inerior of the holder 10, and a spring 28 for thrusting a head 16 of a plunger 15 of the syringe 11 is set in the hinder half part of the holder 10. Further, a start button 21 is disposed on the front end of the holder 10. A needle 14 of the syringe 11 penetrates a through-hole 29 of the end ring 17 and protrudes long forwards. As illustrated in FIGS. 2A and 5, a window 22 through which a capacity scale 12 of the syringe 11 can be read is provided lengthwise at the fore half side surface of the holder 10. Three slots 23, 36 are formed at the hinder half side surface of the holder 10, one 36 of the slots is provided in the upper edge, the recess, of the holder 10 as a route along which a protuberant pin 35 at the upper part of the push piece 25 moves, and the other slots 23 are provided for guiding two pins 33 mounting knobs 24 with which the head 16 of the plunger 15 can be handled from outside of the holder 10 and two pins 34 mounting knobs 26 with which the push piece 25 can be also handled from outside of the holder 10. The means driving the head 16 of the plunger 15 is made up of the push piece 25 and the spring 28. The head 16 of the plunger 15 is in the form of a short cylinder, and is arranged so as to contact with the push piece 25 of the driving means.

The syringe 11 is made of transparent glass likewise to conventional syringes. It is graduated with the capacity scale 12 in the lengthwise direction of the side surface. As shown in FIG. 8A, a fine barrel 13 for sampling a liquid is provided at the center of the interior of the syringe. The injection needle 14 is secured to the front end of the capillary barrel 13, and a plunger 15 can be inserted in the capillary barrel 13.

The capillary barrel 13 of the syringe 11 has its inside diameter determined depending upon the intended quantity of injection. The inside diameter of the syringe 11 is approximately 0.3–1.0 mm. The scale 12 of the syringe 11 has a range of 1-100 $\mu l$, and is graduated with a range of 0.5 $\mu l$.

On the other hand, the holder 10 is a product molded of a hard plastics or a light metal. A thin-walled pipe 27 is inserted in the holder 10 in a manner to extend over the full length thereof. The pipe 27 is made of a metal such as brass and steel and its inner surface is smooth. The pipe 27 is cut away in the same shapes and positions that correspond to the window and the slots of the holder 10. As shown in FIG. 8A, a screw 51 is disposed through a common hole of the holder and the pipe at the rear end of the syringe 11 so as to fix the syringe in the holder.

As shown in FIG. 8A, the end ring 17 is bonded to the front end of the pipe 27. A male screw member 30 having the through-hole 29 is brought into threadable engagement with a female screw portion of the ring 17. A packing 31 is arranged between the male screw member 30 and the syringe 11. As shown in FIG. 8B, a male screw 32 is bonded at the rear of the pipe 27, and the box nut 18 for retaining the driving spring 28 is put thereon. In this manner, the holder 10 is sandwiched and bonded by the ring 17 and the male screw 32.

Further, the upper part 37 of the holder 10 is grooved lengthwise. As shown in FIGS. 3A and 8A, a male screw barrel 39 in such a shape that it is cut away on the recess side is disposed at the front end of the part 37, and a compression spring 41 is arranged in a cavity 40 inside the barrel 39. A lever 43 supported by a fulcrum pin 42 is pivotally mounted in the recess 38 (refer to FIG. 5), and one end of the lever 43 abuts on the upper end of the compression spring 41 situated in the male screw barrel 39, while the other end thereof is inserted under a stepped part 49 of a flat spring 44 disposed on the rear end side of the recess. A female screw barrel 45 which holds the start button 21 in a manner to loosely insert it therethrough is held in threadable engagement with the male screw barrel 39. Accordingly, the front end of the lever 43 is sandwiched between a lower member 21 a of the start button and the compression spring 41, and the start button 21 is normally pushed up as in FIG. 2A by the elastic force of the spring 41. A flat part of the flat spring 44 has a hole 46 for engaging the pin 35 overlying the push piece 25 (refer to FIGS. 3B and 7), and the rear end thereof is fixed to the holder 10 by a screw 47 and a nut 48. Two strips 50 are disposed where the rear end of the lever 43 contacts with the recess 38 so that the end of the lever may not interfere with the movement of the protuberant pin 35 along the slot 36 (FIGS. 2B, 3B and 8B). A locking mechanism is constructed of the hole 46 of the flat spring 44 and the protuberant pin 35 of the push piece 25, while an unlocking mechanism or an injection actuating mechanism is constructed of the start button 21, the compression spring 41, the lever 43 and the stepped part 49 of the flat spring.

V-shaped notches or slits 52 are provided outside the part 37 in the holder. Both the lower edges of the metallic cover 19 are fitted in the slits, to close the upside of the recess 38 and to protect the locking and unlocking mechanisms from being exposed to the exterior.

There will now be explained the operation in the case of injecting the sample liquid into a column of a chromatograph by the use of the apparatus described above.

FIGS. 1 to 7 illustrate the state of the apparatus before and after the injection of the liquid sample. Prior to the injection, a desired volume of the liquid sample is sampled into the syringe 11. The needle 14 of the syringe 11 is immersed into the sample holding the syringe 11 with fingers of one hand, the knobs 24 and 26 are simultaneously moved with fingers of other hand along the slots 23 near the rear end while compressing without locking the spring 28, and then the knobs 24 and 26 are kept apart simultaneously from the fingers. When the sample is introduced into the syring 11, air contained in the needle 14 is accompanied with the sample into the syringe 11. However the air is completely pump out with one or two pumps of such the procedure because the sample is strongly discharged by the elasticity of the spring 28 as the knobs 26 are kept apart from the fingers. After pumping out the air from the syring completely, the knobs 26 are moved along the slots 23 to the rear end immersing the needle 14 of the syringe 11 continuously in the sample. Then the protuberant pin 35 of the push piece is set into the hole 46 of the flat spring 44 so that the spring 28 is locked while compressing the spring. Subsequently the knobs 24 of the head 16 of the plunger 15 are moved along the slots 23 so that the front end of the plunger is brought to the scribe line of the desired volume. Then the desired volume of the sample is completely filled in the syringe 11.

The holder 10 involving the syringe 11 is held in one hand, and the needle 14 of the syringe 11 is inserted being held with the fingers of the other hand through the rubber closure of the injection port of the chromatograph (not shown). The start button 21 is as rapidly pushed down as possible with a finger of the hand holding the syringe 11.

The pushing down of the start button 21 proceeds the following steps at a time to make the locked spring unlock, when the front end of the lever 43 is pushed down by depression of the member 21a, a lower part of the push button 21, the end 49 of the flat spring 44 retained on the rear end of the lever 43 is raised up, resulting in floating of the flat part corresponding to the hole 46 of the flat spring 44 and in releasing the protuberant pin 35 having been held in engagement with the hole 46, so that the locked spring is thereby unlocked. The push piece 25 having been pushed by the spring is forcefully started toward the syringe inside the pipe 27 by the resilience of the spring 28 to collide with the plunger head 16. Since being also quided by the pipe 27, the head 16 is properly advanced without bending the plunger 15.

The discharge of the liquid sample is achieved when the front end of the plunger 15 is stopped at the syringe scale "0". As soon as the sample is discharged, the needle is rapidly withdrawn as possible from the injection port.

After injection, the syringe barrel 13 can be easily and completely washed by twice pumps of the plunger 15 without locking the spring while immersing the needle in a solvent.

Now, the advantages of the apparatus of this invention in use will be described.

The first advantage of this invention is that a desired volume of the liquid sample can be injected at high accuracy and at good reproducibility. The liquid sample is discharged by utilizing the elasticity of the spring, so that the sample is injected into the injection port at high precision in volume. Regarding the precision in eight repeated operations at the quantity of injection exhibiting a recorder response of 90%, the standard deviation is 0.39. Therefore, a substance can be determined by the direct method without using an internal standard substance which is usually used to know the volume of the sample injected.

Figure 10B:
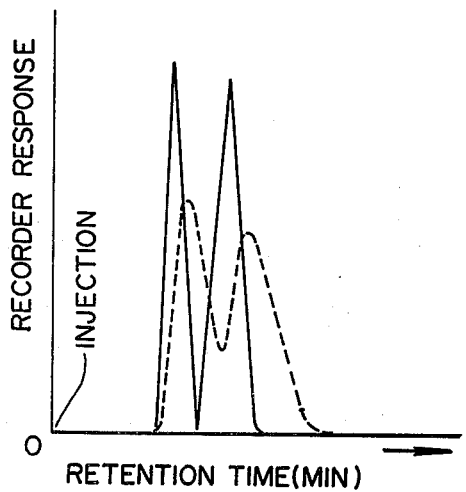
FIG. 10B shows gas-chromatograms obtained by injecting a liquid containing two substances using the devised apparatus and the conventional one.

The second advantage of this invention is that the substances applied to chromatography is separated better using the apparatus than using a conventional syringe. The sample is promtly injected into a chromatograph so that even substances which can not be separated well in the manual injection using the conventional apparatus can be perfectly separated. Especially as regards the separation between low-boiling substances by gas-liquid chromatography, for example, between dichloromethane and methanol, between methanol and iso-propanol, between iso-propanol and ethanol, between ethanol and benzene, different gas-liquid chromatograms are obtained in dependence on the sample injecting method under a chromatographic condition of 25% polyethylene glycole 1000-Diasolid L (60-80 mesh) (3 mm I.D.×3 m), temperature 90° C. or 150° C., and $N_2$ flow rate 40 ml/min. In the conventional injection of above substances, the chromatograms obtained show round peaks and become broad as indicated by dotted lines in FIGS. 10A and 10B, and the separation between two substances is unsatisfactory as indicated by a dotted line FIG. 10A, and the separation between two substances is unsatisfactory as indicated by a dotted line in FIG. 10B. In the injection of the same substances using this invention apparatus, the chromatogram of the substance shows a sharp peak as indicated by a solid line in FIG. 10A, and the separation between two substances is separated better as indicated by a solid line in FIG. 10B.

The third advantage is that a desired volume of the liquid sample can be quickly introduced into the syringe. Ordinarily, when the liquid is introduced into the syringe by backing the plunger, the air which exists in the needle of the syringe is introduced simultaneously. In order to pump out the air from the syringe, the sample liquid is manually discharged with the plunger as vigorously as possible and the pumps are repeated five time or more.

In this invention, when the sample liquid is overfilled into the syringe without locking the spring and the knobs 24 are kept apart from the fingers while immersing the needle of the syringe, the air introduced in the syringe is fully pumped out from within the syringe by twice operations. Accordingly, a desired volume of the liquid sample can be promptly sampled, inducing to reduce time required for analysis by chromatography.

The fourth advantage is that the syringe can be easily and quickly washed, the residual solvent in the syringe thereby being quickly replaced with the sample liquid.

When the sample liquid is manually injected into the chromatograph using the conventional syringe, a large amount of the sample remains in the needle of the syringe. In washing the syringe barrel with a solvent, the residual sample in the needle is introduced close to the plunger when the solvent enters into the syringe because of the capillary barrel of the syringe. Therefore, in pushing out the solvent containing the sample, part of the sample follows to the solvent to be apt to remain in the needle again. In general, twenty to thirty repeated operations are required in order to achieve the manual washing of the syringe.

In this invention, the residual amount of the sample in the needle after the injection is at most 5% of the volume injected because the liquid sample is discharged by the elasticity of the spring. In addition, each pump of the plunger without locking the spring while immersing the needle in a solvent leaves about 5% of the diluted sample left behind. After twice washing, the residual sample in the syringe corresponds to 0.25% of the volume injected, so that the washing may practically be considered as having been completed. Likewise, in sampling the other liquid sample into the syringe after the washing, the residual solvent is promptly substituted with the sample by such the pumps of the plunger without locking the spring. The substitution is usually achieved by twice pumps.

The fifth advantage of this invention is that the barrel of the syringe inserted in the holder composed of the pipe and the molded product of plastics is always free from the heat of the hand grasping the syringe, though the heat usually causes variation of the measurements of the syringe.

The sixth advantage is that the plunger of the syringe is never bent in the pumps in sampling and injection since the head of the plunger is guided by the pipe of the holder.

What I claim is:

1. An apparatus for injecting a desired volume of a liquid in liquid and gas-liquid chromatography comprising:
    a tubular holder defining a lengthwise recess in a wall of an upper part, a cylindrical shell-shaped cover extending over the upper part;
    a syringe positioned within said holder comprising, a needle joined to said syringe protruding outwardly from one end of said holder, a plunger head movable inside said holder longitudinally, said head having pins and guide knobs extending therefrom and a capacity scale formed in a side surface of said syringe;
    driving means positioned within said holder behind said plunger, said driving means including a push piece lying in contact with said plunger head said push piece having a protuberant pin, guide knobs, and guide knob pins attached to said push piece and a spring inserted between said push piece and the other end of said holder;
    a window formed in a side surface of the part of said holder containing said syringe so as to read said capacity scale of said syringe;
    first slots formed in side surfaces of said holder, said guide knobs protruding from sides of said push piece and said plunger head through said first slots;
    a start button disposed at one end of said recess;
    a lever arranged in said recess a portion of which is held in contact with said start button; and
    a mechanism locking said push piece in an urged position and including a flat spring arranged in contact with the other end of said lever in said recess and an hole provided in a flat portion of said flat spring and engaging with said protuberant pin of said push piece.

2. The apparatus for injecting a desired volume of a liquid in liquid and gas-liquid chromatography according to claim 1, wherein a hard pipe which has a smooth inner surface is snugly inserted in said holder, and said pipe is formed with a window and slots which have the same shapes as those of said window and said first slots of said holder.

3. The apparatus for injecting a desired volume of a liquid in liquid and gas-liquid chromatography according to claim 1, including a compression spring for pushing up one end of said lever is contained in opposition to a lower member of said start button.

* * * * *